(12) United States Patent
Radivojevic et al.

(10) Patent No.: US 8,805,517 B2
(45) Date of Patent: Aug. 12, 2014

(54) APPARATUS FOR PROVIDING NERVE STIMULATION AND RELATED METHODS

(75) Inventors: Zoran Radivojevic, Cambridge (GB);
Claudio Marinelli, Cambridge (GB);
Tapani Ryhanen, Cambridge (GB);
Paul Beecher, Cambridge (GB); Piers Andrew, Cambridge (GB)

(73) Assignee: Nokia Corporation, Espoo (FI)

( * ) Notice: Subject to any disclaimer, the term of this patent is extended or adjusted under 35 U.S.C. 154(b) by 792 days.

(21) Appl. No.: 12/316,465

(22) Filed: Dec. 11, 2008

(65) Prior Publication Data
US 2010/0152794 A1 Jun. 17, 2010

(51) Int. Cl.
*A61N 1/18* (2006.01)
*A61N 1/04* (2006.01)

(52) U.S. Cl.
CPC ............ *A61N 1/0412* (2013.01); *A61N 1/0456* (2013.01)
USPC ............................................. 607/46; 607/48

(58) Field of Classification Search
CPC ............................ A61N 1/0412; A61N 1/0456
USPC .................... 607/45, 115, 117, 118, 148, 152
See application file for complete search history.

(56) References Cited

U.S. PATENT DOCUMENTS

| | | | |
|---|---|---|---|
| 4,020,328 A | 4/1977 | Bradam | 235/146 |
| 5,181,030 A | 1/1993 | Itaya et al. | 341/20 |
| 5,709,219 A | 1/1998 | Chen et al. | 128/782 |
| 5,869,791 A | 2/1999 | Young | 178/20.01 |
| 6,655,792 B2 | 12/2003 | Benson et al. | 347/86 |
| 7,111,495 B2 | 9/2006 | Rapp et al. | 73/24.01 |
| 7,176,903 B2 | 2/2007 | Katsuki et al. | 345/173 |
| 7,221,981 B2 * | 5/2007 | Gliner | 607/116 |
| 7,385,443 B1 | 6/2008 | Denison | 330/9 |
| 8,626,283 B1 * | 1/2014 | Zhou | 607/3 |
| 2002/0022873 A1 * | 2/2002 | Erickson et al. | 607/117 |
| 2004/0095330 A1 | 5/2004 | Ling et al. | 345/173 |
| 2004/0131998 A1 * | 7/2004 | Marom et al. | 434/236 |
| 2004/0207542 A1 | 10/2004 | Chang et al. | 341/20 |
| 2005/0131490 A1 * | 6/2005 | Palanker | 607/57 |
| 2005/0187454 A1 | 8/2005 | Gabl et al. | 600/372 |
| 2006/0061545 A1 | 3/2006 | Hughes et al. | 345/156 |
| 2006/0085049 A1 * | 4/2006 | Cory et al. | 607/48 |
| 2006/0085056 A1 * | 4/2006 | Schouenborg | 607/148 |
| 2006/0149341 A1 * | 7/2006 | Palti | 607/63 |

(Continued)

FOREIGN PATENT DOCUMENTS

| | | |
|---|---|---|
| EP | 2 000 885 A1 | 12/2008 |
| JP | 2005/276089 A | 10/2005 |

(Continued)

OTHER PUBLICATIONS

"Capacitively Coupled Electromagnetic Field Therapy as a Treatment Modality in Veterinary Medicine" http://www.scitechvet.com/articles.html, retrieved Dec. 30, 2008.

(Continued)

*Primary Examiner* — Christopher D Koharski
*Assistant Examiner* — Natasha Patel
(74) *Attorney, Agent, or Firm* — Harrington & Smith

(57) ABSTRACT

An apparatus includes an optically transparent electrode configured to provide transcutaneous electrical nerve stimulation to a user contacting a portion of an exterior surface of the apparatus proximal to the optically transparent electrode.

56 Claims, 10 Drawing Sheets

(56) References Cited

U.S. PATENT DOCUMENTS

| | | | |
|---|---|---|---|
| 2006/0241718 A1* | 10/2006 | Tyler et al. | 607/45 |
| 2008/0157893 A1 | 7/2008 | Krah | 331/177 R |
| 2008/0255434 A1* | 10/2008 | Hayter et al. | 600/309 |
| 2009/0002328 A1 | 1/2009 | Ullrich et al. | 345/173 |
| 2009/0079550 A1 | 3/2009 | Makinen et al. | 340/407.2 |
| 2009/0085878 A1 | 4/2009 | Heubel et al. | 345/173 |
| 2009/0128503 A1 | 5/2009 | Grant et al. | 345/173 |
| 2009/0167704 A1 | 7/2009 | Terlizzi et al. | 345/173 |
| 2009/0174671 A1 | 7/2009 | Tachi et al. | 345/173 |
| 2009/0243632 A1 | 10/2009 | Ozawa | 324/679 |
| 2009/0293631 A1 | 12/2009 | Radivojevic | 73/774 |
| 2009/0322496 A1 | 12/2009 | Da Costa | 340/407.2 |
| 2010/0079403 A1 | 4/2010 | Lynch et al. | 345/173 |
| 2010/0085169 A1 | 4/2010 | Poupyrev et al. | 340/407.2 |
| 2010/0152794 A1 | 6/2010 | Radivojevic et al. | 607/2 |
| 2010/0231550 A1 | 9/2010 | Cruz-Hernandez et al. | |
| 2010/0265210 A1 | 10/2010 | Nakanishi et al. | 345/174 |
| 2011/0032088 A1 | 2/2011 | Kim et al. | 340/407.1 |
| 2011/0037707 A1 | 2/2011 | Radivojevic et al. | 345/173 |
| 2011/0079449 A1 | 4/2011 | Radivojevic | 178/18.03 |
| 2011/0127880 A1 | 6/2011 | Murphy et al. | 310/317 |
| 2011/0279250 A1 | 11/2011 | Ryhanen et al. | 340/407.2 |
| 2011/0286156 A1 | 11/2011 | Beecher et al. | 361/679.01 |
| 2012/0038559 A1 | 2/2012 | Radivojevic et al. | 345/173 |
| 2012/0293441 A1 | 11/2012 | Eldering | 345/173 |

FOREIGN PATENT DOCUMENTS

| | | |
|---|---|---|
| JP | 2008/532564 A | 8/2008 |
| WO | WO 87/07825 | 12/1987 |
| WO | WO 2006/041648 | 4/2006 |
| WO | WO 2007/010441 | 1/2007 |
| WO | WO 2008/037275 | 4/2008 |
| WO | WO 2009/037379 A1 | 3/2009 |
| WO | WO 2009/141502 A1 | 11/2009 |
| WO | WO 2009/158074 A1 | 12/2009 |
| WO | WO 2010/066817 A2 | 6/2010 |
| WO | WO 2010/124683 A1 | 11/2010 |

OTHER PUBLICATIONS

"induced Current Constraints and Capacitive Effects in Inductive Nerve Stimulation"—McCarthy S, Haradem D, IEEE Transactions on Biomedical Engineering, vol. 37, Issue 6, Jun. 1990, pp. 598-605, http://ncbi.nlm.nih.gov/pubmed/2354841.

"Noninvasive Neuroelectronic Interfacing with Synaptically Connected Snail Neurons Immobilized on a Semiconductor Chip", Gunther Zeck, Peter Fromherz, PNAS Aug. 28, 2001 vol. 98 No. 18 10457-10462, http://www.pnas.org/content/98/18/10457.full.pdf+html.

"Capacitive Stimulatory Effect in Magnetic Stimulation of Nerve Tissue" Ueno S. Matsumoto S, Harada K, Oomura Y, IEEE Transactions on Magnetics, vol. 14, Issue5, Sep. 1978 pp. 958-960, http://ieeexplore.ieee.org/stamp/jsp?arnumber+01059800.

http://venturebeat.com/2008/05/30/startup-senseg-promises-game-changing-tactile-technology/—retrieved Jan. 12, 2009.

Nice, K. et al., "How Digital Cameras Work", Nov. 29, 2006, HowStuffWorks.com, <http://electronics.howstuffworks.com/cameras-photography/digital/digital-camera.htm> Feb. 19, 2013, p. 1-6.

Bao, Oliver et al., "Teslatouch: Electrovibration for Touch Surfaces", (Oct. 4, 2010), (10 pages).

Peter B.L. Meijer, "Augmented Reality for the Totally Blind", Nov. 2010, (4 pages).

Yamamoto, et al., "Electrostatic Tactile Display with Thin Film Slider and Its Application to Tactile Telepresentation Systems", IEEE Transactions on Visualization and Computer Graphics, vol. 12, No. 2, (Mar./Apr. 2009), (pp. 168-177), XP003026562.

Kaczmarek, et al., "Polarity Effect in Electrovibration for Tactile Display", NIH Public Access. Author Manuscript, IEEE Trans Boimed, (Oct. 2006), (pp. 1-17).

"Series E: Overall Network Operation, Telephone Service, Service Operation and Human Factors", ITU-T Recommendation E.161, Telecommunication Standardization Sector of ITU, Feb. 2001, 14 pgs.

http://www.nokia.com/about-nokia/research/demos/the-morph-concept; "Develop for Lumia", Feb. 25, 2014, 9 pgs.

* cited by examiner

APPARATUS FOR PROVIDING NERVE STIMULATION AND RELATED METHODS

FIELD

This specification relates to apparatuses for providing electrical nerve stimulation and to related methods.

BACKGROUND

Touch-screen displays are known in the field of electrical consumer goods.

SUMMARY

This specification provides an apparatus comprising an optically transparent electrode configured to provide transcutaneous electrical nerve stimulation to a user contacting a portion of an exterior surface of said apparatus proximal to said optically transparent electrode.

This specification also provides an apparatus comprising a substrate, a two-dimensional array of electrodes supported on said substrate, and a stimulation circuit configured such as selectively to provide a nerve stimulation potential to one or more of said electrodes.

This specification also provides a method comprising using an optically transparent electrode to provide transcutaneous electrical nerve stimulation to a user contacting a portion of an exterior surface of said apparatus proximal to said optically transparent electrode.

This specification also provides a method of operating a two-dimensional array of electrodes supported on a substrate, comprising selectively providing a nerve stimulation potential to one or more of said electrodes.

This specification also provides a method comprising providing a first substrate layer, forming a plurality of depressed regions in said first substrate layer, forming a first plurality of conducting tracks on said first substrate layer, providing a second substrate layer in said depressed regions, forming a second plurality of conducting tracks on said second substrate layer, providing a third substrate layer on said second substrate layer and on said second plurality of conducting tracks.

This specification also provides a method comprising providing a mould with a plurality of protuberances formed thereon, forming a first plurality of conducting tracks on said mould, providing a first substrate layer on regions of said mould between said protuberances, forming a second plurality of conducting tracks on said first substrate layer, providing a second substrate layer on said first substrate layer and on said second plurality of conducting tracks, removing said mould, providing a third substrate layer in a volume vacated by said removed mould.

DETAILED DESCRIPTION OF EMBODIMENTS

Figure 1A:
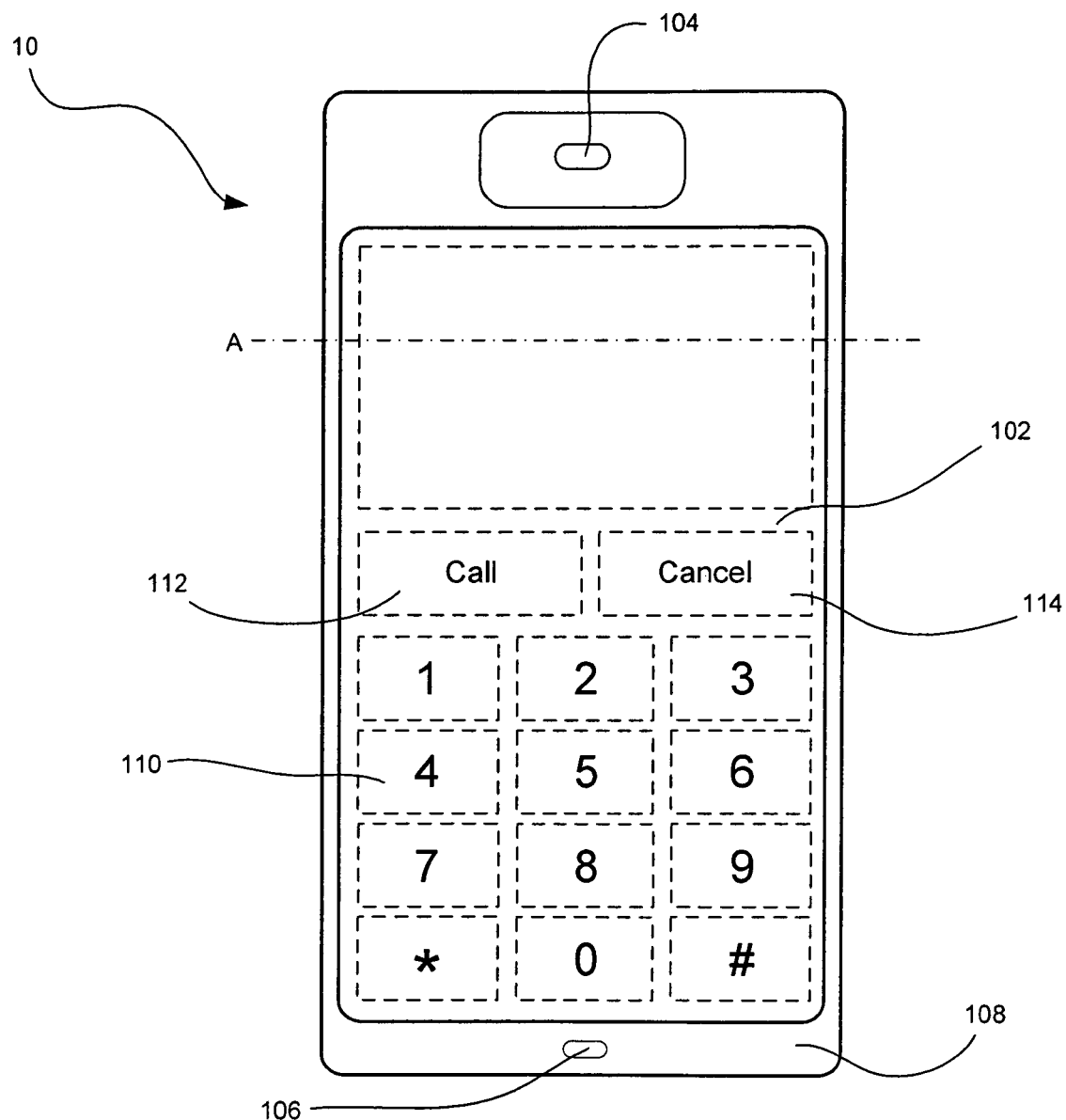
FIG. 1A is a plan-view of an electronic device.

In the drawings, like reference numerals denote like elements.

FIG. 1A depicts a plan-view of an electronic device 10, in this example a mobile phone. The mobile phone 10 comprises a display 102, a speaker 104, a microphone 106, and a housing 108. The display 102 is a touch-sensitive display. In the Figure, the display 102 is displaying a dialing user interface comprising a number of selectable options, including numbers 110, a call function 112 and a cancel function 114. To select an option, the user touches an outer surface 116 (see FIG. 1B) of the display 102 at a location corresponding to the desired option.

Figure 1B:
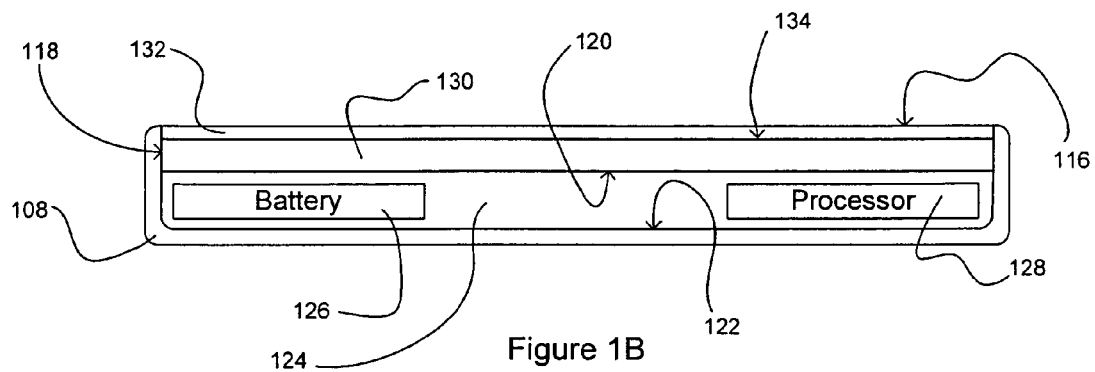
FIG. 1B is a schematic cross-sectional view through the electronic device of FIG. 1A.

FIG. 1B depicts a schematic cross-sectional view through the mobile phone 10, at the line denoted A in FIG. 1A. The housing 108 surrounds the side surfaces 118 and rear surface 120 of the display 102. The inner surface 122 of the housing 108 and the rear surface 120 of the display 102 define an internal volume 124 of the mobile phone 10. The internal volume 124 houses a battery 126 and a processor 128. The battery 126 supplies power to the processor 128 and the display 102. The processor 128 is adapted to the control the operation of the display 102.

The display 102 comprises a display panel 130 and a touch sensitive tactile feedback (TSTF) layer 132.

The display panel 130 comprises an LCD display panel, the operation and construction of which are well known in the art. It should be understood, however, that other types of display panel may be used instead.

The TSTF layer 132 overlies an upper surface 134 of the of the display panel 130. The TSTF 132 layer is operable to detect tactile input by a finger of a user touching an outer surface 116 of the TSTF layer 132. The TSTF layer 132 is operable also to provide tactile feedback to the finger of a user touching the outer surface 116 of the TSTF layer 132.

Figure 1C:
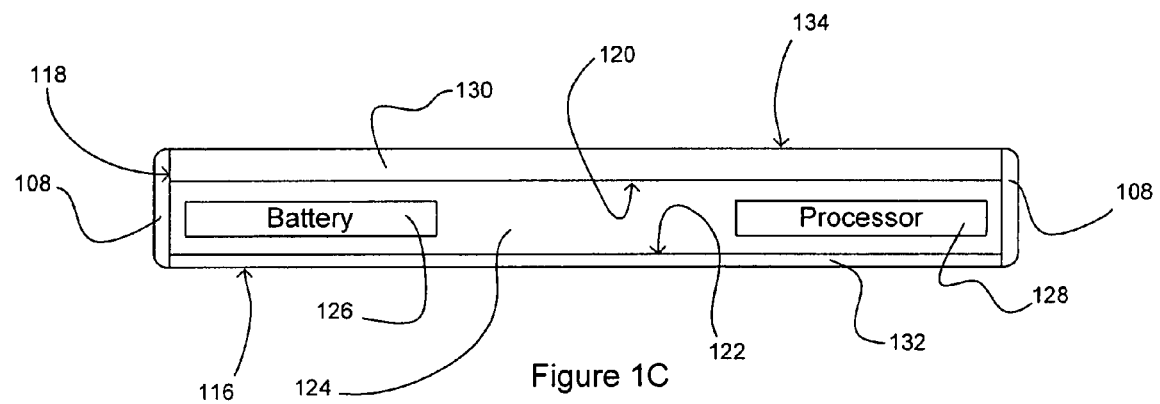
FIG. 1C is a schematic cross-sectional view through the electronic device of FIG. 1A according to alternative embodiments.

FIG. 1C depicts a schematic cross-sectional view through the mobile device 10 according to an alternative embodiment. In this embodiment, the TSTF layer 132 is provided on a surface of the device 10 opposite to the surface on which the display panel 130 is located. The TSTF layer is operable to detect tactile input by a finger of a user touching an outer surface 116 (in FIG. 1C, the lower surface) of the TSTF layer 132. The TSTF layer 132 is operable also to provide tactile feedback to the finger of a user touching the outer surface 116 of the TSTF layer 132.

It will be understood that the TSTF layer 132 may be provided in or on any exterior surface of the mobile device 10. For example, the TSTF layer may be located on the side of a device to replace a tracker wheel. Also, it will be understood that the mobile device 10 may comprise more than one TSTF layer 132. For example, one TSTF layer may be located above the display of the device and another may be located on the rear of the device 10.

A user of the device of FIG. 1C may provide touch inputs by touching an area of the TSTF layer 132 that corresponds to a selectable option displayed on a region of the display panel 130.

Figure 2:
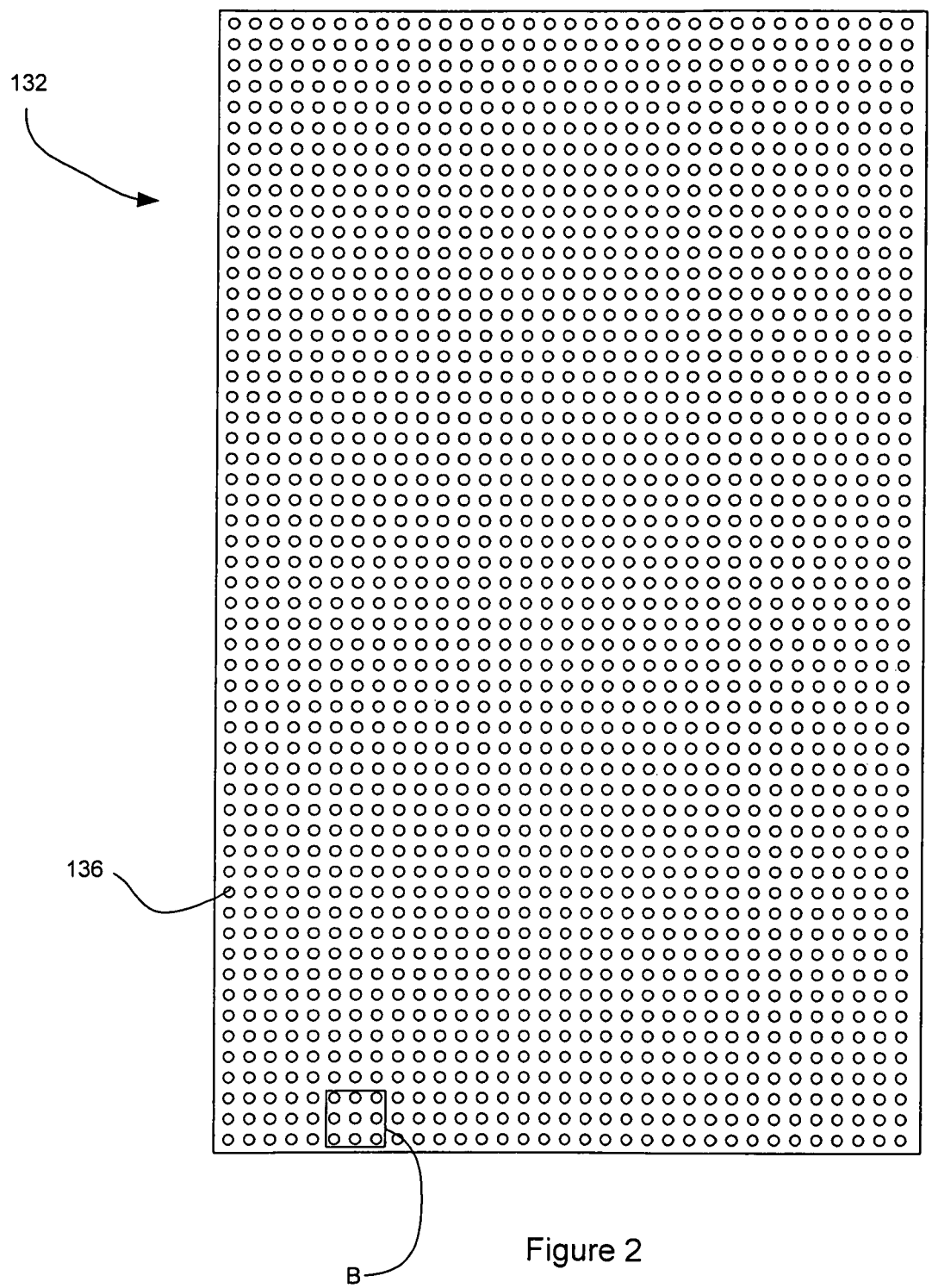
FIG. 2 is a simplified schematic plan view of a component of the electronic device of FIG. 1.

FIG. 2 depicts a simplified schematic plan view of the TSTF layer 132. The TSTF layer 132 comprises a plurality of electrodes 136 arranged in a grid array. Each of the electrodes 136 is individually operable to detect a tactile input by a finger of a user touching an outer surface 116 of the TSTF layer 132. Each of the electrodes is individually operable also to provide tactile feedback to the finger of a user touching the outer surface 116 of the TSTF layer 132.

The TSTF layer 132 is optically transparent. As such, visible light can pass through the TSTF layer 132 with little or no diffusion. An image displayed by the display panel 130 underlying the TSTF layer 132 is clearly visible to the user. It will be understood that, as the TSTF layer 132 as a whole is optically transparent, its constituent parts are also optically transparent. As such, the electrodes 136 are optically transparent. It will be appreciated that a TSTF layer 132 that is not located above the display panel 130, such as in FIG. 1C, may instead be optically opaque or translucent.

Figure 3A:
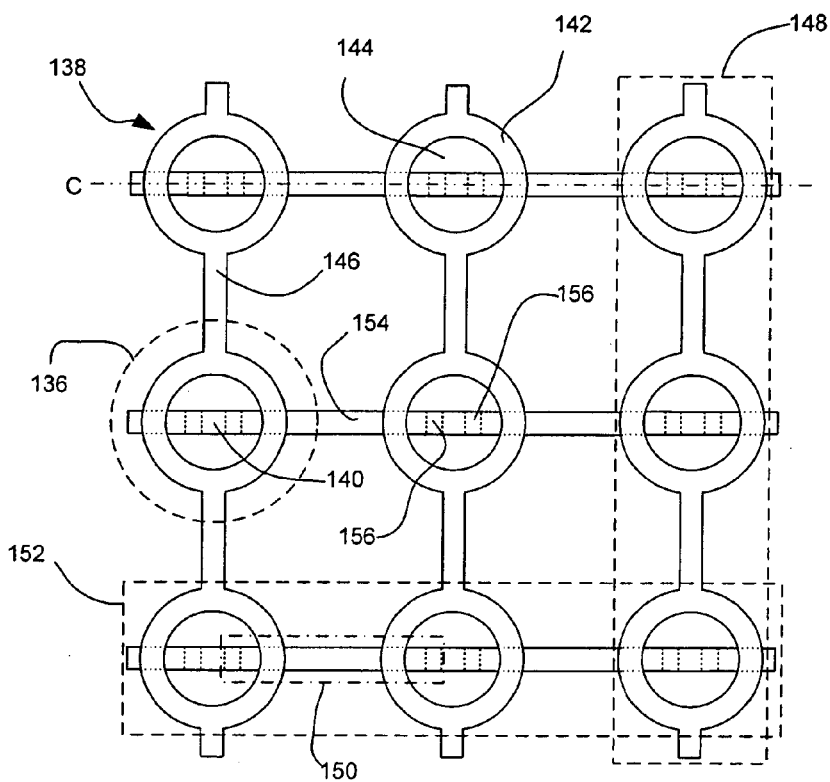
FIG. 3A is a magnified view of a region of the component of FIG. 2.
Figure 3B:
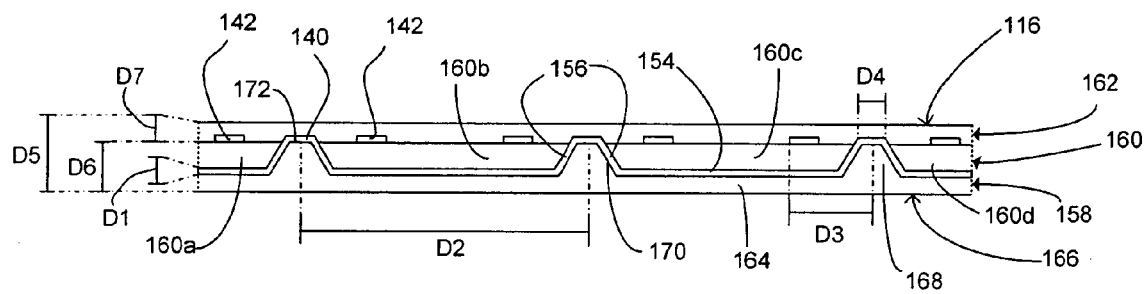
FIG. 3B is a cross-sectional view through the region shown in FIG. 3A.

FIG. 3A shows the region of the TSTF layer 132 denoted B in FIG. 2. FIG. 3B is a cross-sectional view of the region B of the TSTF layer 132, along the line denoted C in FIG. 3A. Each of the plurality of electrodes 136 is comprised of a first electrode element 138 and a second electrode element 140. The first electrode element 138 has a conducting region 142, surrounding a vacant region 144. The conducting region 142 is annular. The second electrode element 140 is located at the centre of the vacant region 144 of the first electrode element 138. The second electrode element 140 is square. The first and second electrode elements 138, 140 have their centres at approximately the same point.

Each of the first electrode elements 138 of each of the electrodes 136 is connected to the first electrode elements 138 of two adjacent electrodes 136 by first connecting elements 146. In this way, columns 148 of first electrode elements 138 are connected in series. These columns 148 of connected first electrode elements 138 extend across the entire length of the TSTF layer 132. It will be understood that the first electrode elements 138 at either end of each column 148 are connected to just one other first electrode element 138.

Each column 148 of first electrode elements 138 is connected at either end to a first power supply (not shown). The first power supply is operable to provide a potential to each of the columns of first electrode elements 138 individually. The first power supply provides power derived from the battery 126. It will be understood that, in a device that has an alternative power source, the first power supply may provide power derived from the alternative power source. An alternative power supply may be, for example, a transformed mains electricity supply such as may be received at a charging input.

Each of the first electrode elements 138 and each of the first connecting elements 146 are in a first plane, as is clear from FIG. 3B. In FIG. 3A, the first plane is parallel to the plane of the page, and in FIG. 3B, the first plane is perpendicular to the plane of the page.

Each of the second electrode elements 140 of each of the electrodes 136 is connected to the second electrode elements 140 of two adjacent electrodes 136 by second connecting elements 150. In this way, rows 152 of second electrode elements 140 are connected in series. These rows 152 of connected second electrode elements 140 extend across the entire width of the TSTF layer 132. It will be understood that the second electrode elements 140 at either end of each row 148 are connected to just one other second electrode element 140.

Each of the second connecting elements 150 comprises a planar portion 154 and two intermediary portions 156. The second electrode elements 140 are in a different plane to the planar portions 154 of the second connecting elements 150. The second electrode elements 140 are substantially in the first plane. This is the plane in which the first electrode elements 138 lie. It will be understood that the first and second elements may alternatively not be in the same plane. The planar portions 154 of the second connecting elements 150 are located in a second plane that is substantially parallel to the first plane. The second plane is further from the outer surface 116 of the TSTF layer 132 than the first. As such, the second connecting elements 150 pass beneath the first electrode elements 138.

Each of the two intermediary portions 156 of each of the second connecting elements 150 connects the planar portion 154 of the second connecting element with a second electrode element. The intermediary portions 156 extend between the first plane and the second plane.

Each column 148 of first electrode elements 138 is connected at either end to a first power supply (not shown). Each row 152 of second electrode elements 140 is connected at either end to a second power supply (not shown). The first power supply is operable to provide a potential to each of the columns of first electrode elements 138 individually. The second power supply is operable to provide a potential to each of the rows of second electrode elements 140 individually. The first and second power supplies provide power derived from the battery 126. It will be understood that, in a device that has an alternative power source, the first and second power supplies may provide power derived from the alternative power source. An alternative power supply may be, for example, a converted mains electricity supply.

The columns 148 of first electrode elements 138 and the rows 152 of second electrode elements 140 are substantially perpendicular to one another. However, they may instead be arranged non-perpendicularly.

The electrodes 136 are individually operable to provide electro-stimulation to the nerves in the finger tips of a user. It will be understood that the electrodes also may be individually operable to provide electro stimulation to any location on a user's skin, for example, but not limited to, the skin on or above the wrist.

The distance D2 between the electrodes 136 may be in the sub-millimeter to millimeter range. The distance D2 may for example in the range of 0.1 mm to 5 mm. Advantageously, the distance D2 may be for example in the range of 0.1 mm to 1 mm. The distance D2 may be for instance in the range of 0.1 mm to 0.5 mm. The density of receptors in a finger tip is such that this spacing allows a user to detect electro-stimuli from two separate electrodes 136. At this spacing D2 between the electrodes 136, the radius D3 of the annular first electrode elements 138 may be in the region of, or slightly less than D2/4, for instance 100 μm, and the width D4 of the second electrode element may be in the region of, or slightly less than D2/8, for instance 50 μm.

The TSTF layer 132 is comprises three sub-layers: a first sub-layer 158, a second sub-layer 160, and a third sub-layer 162.

The first sub-layer 158 comprises a base portion 164 having a uniform thickness. The bottom surface 166 of the base portion 164 constitutes, or forms, the bottom surface 166 of the TSTF layer 132. Extending from an upper surface 168 of the base portion 164 is a plurality of ridges 168 having a substantially trapezoidal profile. It will be understood that the plurality of ridges 168 instead may have another profile shape, for example, but not limited to, hemispherical. It will be appreciated that as long as the rows 152 of second electrode elements 140 can be provided on the upper surface of the ridges 168, the exact shape of the ridges 168 may not be important.

Instead of the second electrode elements 140 being provided on ridges 168 in the first sub-layer 158, the second electrode elements may be provided on non-elongate protuberances. For example, the protuberances may be three-dimensional trapezoids, or truncated square-based pyramids, extending from the base portion 164 of the first sub-layer 158. Consequently, in this embodiment, the first sub-layer 158 may comprise a flat base portion 164 having a two-dimensional array of protuberances for receiving the second electrode elements 140. The second sub-layer 160 may be provided on the regions of the base portion 164 surrounding the two-dimensional array of protuberances. The second sub-layer 160 may extend to the approximately the height of the protuberances. The protuberances may be periodically or aperiodically spaced.

The ridges 168 are equidistant from one another. It will be understood, however, that the spacing between the ridges 168 may instead not be uniform, but may vary. For example, the ridges 168 may be provided such that the first sub-layer 158 comprises a plurality of periodically or aperiodically spaced groups of ridges 168. In this way, the groups of periodically or aperiodically spaced electrodes 136 may be provided. The ridges 168 extend across the entire length of the first sub-layer 158.

Figure 4A:
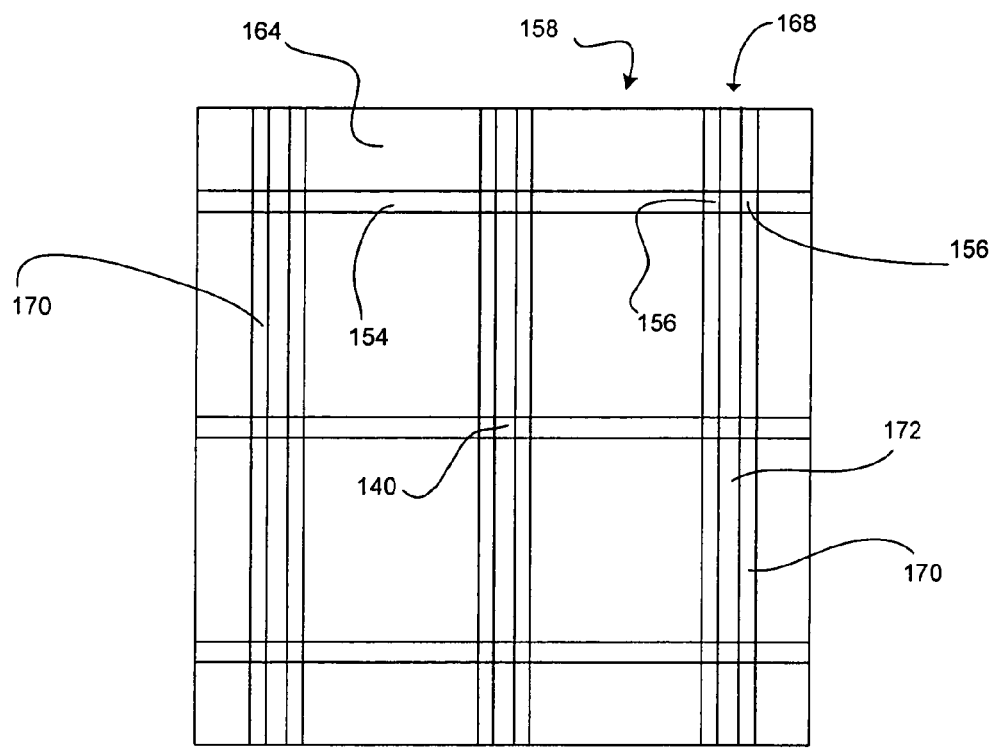
FIG. 4A is a plan-view of first sub-layer of the region of the component shown in FIG. 3A.

The rows 152 of second electrode elements 140 are provided on an upper surface of the first sub-layer 158. The rows 152 of the second electrode elements 140 are perpendicular to the longitudinal axes of the ridges 168. The planar portions 154 of the second connecting elements 150 are located on the upper surface 168 of the base portion 164 in the regions between the ridges 168. The intermediary portions 156 are located on the inclined sides 170 of the ridges 168. The second electrode elements 140 are located on the upper surfaces 172 of the ridges 168. FIG. 4A depicts a plan-view of the first sub-layer 158 with the rows 152 of connected second electrode elements 140 situated thereon. The rows 152 of second electrode elements 140 are equidistant from one another. It will be understood, however, that the spacing between the rows 152 may instead not be uniform, but may vary. For example, the rows 152 may be provided in pluralities of periodically or aperiodically spaced groups of rows 168. In this way, the groups of periodically or aperiodically spaced electrodes 136 may be provided.

Figure 4B:
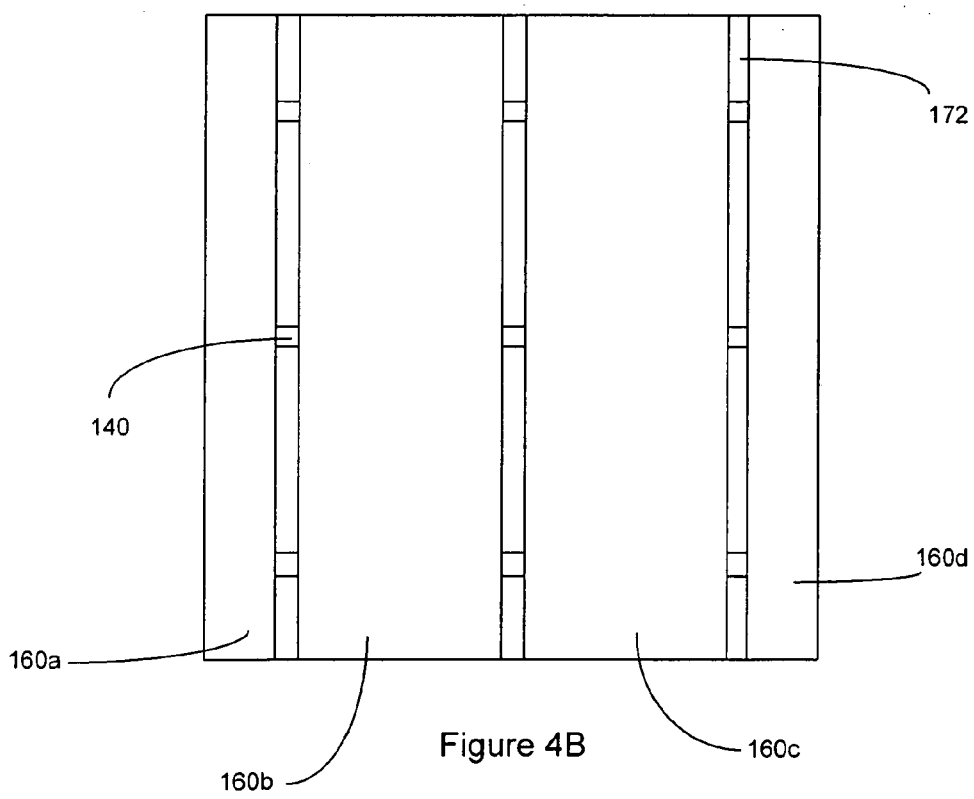
FIG. 4B is a plan-view of first and second sub-layers of the region of the component shown in FIG. 3A.

The second sub-layer 160 is provided in the regions between the ridges 168 of the first sub-layer 158. The second sub-layer 160 extends from the base portion 164 of the first sub-layer 158 to approximately the height of the tops 172 of the ridges 168 of the first sub-layer 158. Consequently, the second sub-layer 160 comprises separate distinct regions 160a, 160b, 160c, 160d, between the ridges 168. The separate regions 160a, 160b, 160c, 160d of the second sub-layer 160 have a substantially trapezoidal profile, as can be seen in FIG. 3B. It will be understood that the plurality of ridges 168 instead may have another profile shape, for example, but not limited to, hemispherical. FIG. 4B shows a plan-view of the first and second sub-layers 158, 160 and the second electrode elements 140 located thereon.

The columns 148 of first electrode elements 138 (not shown in FIG. 4B) are provided on the upper surface 172 of the second sub-layer 160 in a direction perpendicular to the rows 152 of connected second electrode elements 140. It will be appreciated, however, that the rows 152 and columns 148 instead may not be perpendicular to one another, but may be provided at a different angle to one another.

The third sub-layer 162 is provided atop the second sub-layer 160 having the columns 148 of connected first electrode elements 138 provided thereon. The third sub-layer 162 has a flat upper surface, which constitutes the outer surface 116 of the TSTF layer 132.

The columns 148 of connected first electrode elements 138 comprise an electrically conducting material. The rows 152 of connected second electrode elements 140 comprise an electrically conducting material. The columns 148 of connected first electrode elements 138 and the rows 152 of connected second electrode elements 140 comprise an optically transparent material. Suitable materials include, but are not limited to, carbon nanotube networks (CNTNs), an indium-titanium-oxide (ITO) film, wide bandgap oxides, for example zinc oxide, provided in thin transparent layers, and thin layers of gold or silver. It will be appreciated that on a microscopic scale these materials may not be optically transparent. However, on the macroscopic scale of interest, these materials are sufficiently transparent to enable the user to see clearly images displayed on the display panel 130 through the TSTF layer 132. The thickness D1 (see FIG. 3B) of the connected first and second electrode elements 136, 140 may be in the range of nanometers to microns For instance, the thickness D1 may be in the range 20 nm to 100 nm. It will be understood that other values of D1 may instead be suitable.

The three sub-layers, 158, 160, 162 of the TSTF layer 132 are optically transparent. The first and second sub-layers 158, 160 comprise electrically insulating, dielectric materials. Suitable materials for the first and second sub-layers 158, 160 include, but are not limited to, silicone, polyimide, poly (metyl methacrylate) (acrylic glass), polystyrene, polycarbonate, polyethylene naphthalate, or polyethylene terephthalate.

The materials of the sub-layers may be chosen such as to provide effective refractive index (RI) matching between the TSTF layer 132 and the display panel 130. The materials of the sub-layers may be chosen also such as to provide effective refractive index (RI) matching between the sub-layers themselves. This can optimise the transmission of light through the TSTF layer 132. It may be beneficial, to utilise the same material for different sub-layers where possible. Suitable materials tend to have refractive indexes of approximately 1.5 so as to match the RI of the optical glass commonly used in display panels (the RI of silicone is between 1.38 and 1.6, the RI of PMMA=1.59).

The third sub-layer 162 is electrically insulating. This ensures electrical isolation of the electrodes from the user's fingers. In this way, the effect on the operation of the device due to a user having wet or dirty fingers may be reduced. The third sub-layer 162 has properties that protect the electrodes 136 from the outside environment. These properties may include, but are not limited to, being hydrophobic, being self-cleaning, being scratch resistant, and being oil/grease repellent. A self-assembled monolayer coating may be deposited on the outer surface 116 of the third sub-layer 162. In this way the third sub-layer 162 may exhibit both hydrophobicity and oleophobicity. Alternatively, the outer surface 116 may be microscopically or nanoscopically rough. This reduces the contact area for contaminants or alien matter on the outer surface 116. Alternatively, the third sub-layer 162 may be made capable of performing photocatalytic and hydrophilic processes. This may be achieved in any suitable way. The third sub-layer 162 may be comprised of, for example, silicone, polyimide, poly(metyl methacrylate) (acrylic glass), polystyrene, polycarbonate, polyethylene naphthalate, or polyethylene terephthalate.

The overall thickness D5 of the TSTF layer 132 may be in the range of microns to millimeters. For instance, the overall thickness D5 of the TSTF layer 132 may be in the range of 50 µm to 300 µm. The combined thickness D6 of the first and second sub-layers 158, 160 may be slightly less than the thickness D5. It will be understood, however, that D6 must necessarily be less than D5. The third sub-layer 162 may have a thickness D7 in the sub-micron to microns range. The thickness D7 of the third sub-layer 162 is limited by the requirement for efficient capacitive coupling to the user's skin. The value of D7 may be in the range of 500 nm to 2 µm. It will be understood that other thicknesses may also be suitable whilst providing the desired effects of optical transparency for the TSTF layer, the ability to detect touch inputs and the ability to provide tactile feedback to the user.

By enclosing the electrodes 136 between the first and third sub-layers 158, 162, the electrodes may protected from corrosion, abrasion, erosion and the like. Consequently, the TSTF layer 132 is relatively durable.

Figure 3C:
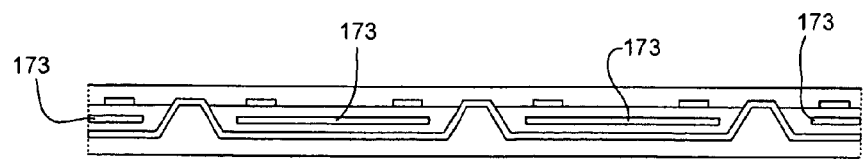
FIG. 3C is a cross-sectional view through the region shown in FIG. 3A according to alternative embodiments.

FIG. 3C is a cross-sectional view through the region shown in FIG. 3A according to alternative embodiments. In FIG. 3C, the TSTF layer additionally comprises guard electrodes 173. Other components of the Figure are the same as that shown in FIG. 3B, although reference numerals are omitted. Guard electrodes 173 may enhance the performance of the input detection functionality of the TSTF layer 132 by counteracting parasitic capacitive coupling between the first and second connecting elements.

The guard, or grounding, electrodes 173 are located between the first plane, in which the first and second electrode elements 148, 140 are substantially located, and the plane in which the second connecting elements 150 lie. In these embodiments, the second sub-layer 160 may be provided in two sections. The first section may extend from the first sub-layer 158 to approximately half the height of the ridges 168 or protuberances. The guard electrodes 173 may be provided atop the first section of the second sub layer 160. The second section of the second sub-layer 160 may be provided atop the guard electrodes 173. The guard electrodes 173 are electrically isolated from the columns and rows of first and second electrodes elements by the second sub layer 160. The guard electrodes 173 are located in regions of the TSTF layer 132 between the plurality of ridges 168. The guard electrodes 173 may be grounded.

In embodiments comprising plural protuberances instead of ridges 168, the guard electrodes 173 are located in the regions of the TSTF layer 132 between the protuberances. In these embodiments, the guard electrodes 173 may be formed of a single layer of conducting material provided across the entire area of the TSTF layer 132, but having empty regions surrounding the protuberances. The empty regions may be shaped according to the shape of the protuberances. The guard electrodes 173 may be grounded.

According to alternative embodiments, the guard electrode may be sub-divided. In these embodiments the guard electrodes may be provided with a offset potential that may be dynamically controlled.

The TSTF layer 132 is operable to detect touch inputs as a result of capacitive coupling between the electrodes 136 and the finger tip of a user. Referring again to FIG. 3B, it can be seen that the first electrode elements 138 are separated from their respective second electrode elements 140 by a region of dielectric material. It will be understood that, when a potential difference is applied across the first and second electrode elements 138, 140, an effective capacitor, having a detectable capacitance, is formed. When a finger tip is applied to the outer surface 116 of the TSTF layer 132, the finger tip is separated from the first and second electrode elements 138, 140 by a region of dielectric material (the third sub-layer 162). Consequently, because the finger tip has a potential that is different to at least one of the electrode elements 138, 140 a capacitor is formed between the at least one electrode elements 138, 140 and the finger tip. It will be understood that the finger tip may capacitively couple with plural electrodes simultaneously. The capacitance between the electrode 136 and the finger tip results in a change to the value of the capacitance between the first and second electrode elements 138, 140 and thus the corresponding row 152 and column 148. One or more transistor circuits (not shown) are switchably connected with each row and with each column. These circuits are operable to detect capacitance changes experienced at particular row and column combinations. The transistor circuits (not shown) are connected to the processor 128, which is configured to perform calculations based on outputs of the transistor circuits so as to determine the row and column combinations that experience contact by a finger tip.

It will be understood that, alternatively, systems not including transistors may be used to detect capacitance changes at one or more of the electrodes.

In this way the processor 128 is operable to identify at least one electrode 136 experiencing a change in capacitance. In this way, the processor is operable to detect a touch input incident on the surface of the TSTF layer 132, and to determine its location, based at least partially on the location of the electrode or electrodes experiencing an altered capacitance.

The touch sensitive functionality of the TSTF layer 132 may also allow the device to provide finger print scanning functionality. Finger tips are comprised of unique patterns of ridges and depressions. Consequently, when a finger tip is in contact with the outer surface 116 of the TSTF layer 132, it is only the ridges of the finger tip that are in contact with the surface 116, whereas the depressions are separated by a small distance. The electrodes 136 that are under a ridge of the finger tip will experience a different change in capacitance to those under a depression. Therefore, provided that the separation of the electrodes 136 in the TSTF layer 132 is less than the distance between ridges in the finger tip, which may be approximately 0.5 mm, the TSTF layer 132 allows detection of the finger print of a user. Electrode separation D2 of approximately 150 µm is suitable to enable the device to perform finger print scanning. It will be appreciated that the provision of finger print scanning functionality in a device, such as a mobile phone, can allow greatly enhanced security capabilities. These security capabilities may include features such as fingerprint locking and unlocking of the mobile device, fingerprint locking or unlocking of private documents stored on the device. The security capabilities may also include features such as secure icon applications, which may be graphical images displayed on the display panel and representing selectable options which can be selected/executed only subsequent to an input by a recognised and/or authorised fingerprint. Also, the incorporation of fingerprint scanning functionality into the mobile device via the TSTF layer 132, removes the need for an additional fingerprint scanner to be provided. This reduces the overall cost and bill of materials associated with manufacturing a mobile device that includes a finger print scanning functionality.

The TSTF layer 132 is also operable to provide tactile feedback to a user of the mobile phone 10. Tactile feedback is provided to a user by utilising the capacitive coupling between an electrode 136 and the finger tip. As discussed above in relation to the detection of touch inputs, when a finger tip is applied to the outer surface 116 of the TSTF layer 132, the finger tip capacitively couples with an electrode/electrodes underlying the finger tip. The capacitive coupling results in an electrical charge being induced in nerve endings in the finger tip of the user. The charge induced in the nerve endings is dependent on the potential difference between the first and second electrodes 138, 140. The charge induced in the nerve endings, if sufficiently large, can provide a tactile sensation to the user. A potential difference suitable for providing a charge of sufficient magnitude in the nerve endings of a user is about, or slightly less than, 10 V. This is known as transcutaneous electrical nerve stimulation (TENS). Transcutaneous, or transdermal, stimulation occurs by way of, or through, the skin. A user may calibrate the intensity of tactile stimulation by increasing or decreasing the stimulating potential difference until an optimal tactile stimulation is perceived. This may be achieved by a calibration function which may for instance be accessed through a menu system of the mobile device.

This nerve stimulation may be utilized in a number of different ways. It may be used to provide feedback to a user. Following detection of a touch input via the TSTF layer 132, the TSTF layer 132 is controlled by the processor 128 to activate the electrodes 136 at which the touch input was received to provide stimulation of the nerves in the finger tip of the user. Consequently, the user becomes aware that the touch input has been registered by the device 10.

The tactile feedback provided by the TSTF layer 132 is highly localised in the sense that only the relevant electrodes 132 are controlled to provide tactile stimulation. This results in reduced power expenditure when compared to mechanisms that cannot provide localised tactile feedback. Also, the TSTF layer 132 may be more energy efficient when compared to devices that use piezoelectric or electromagnetic actuators to provide monolithic mechanical vibration of the device. Moreover, devices that utilise mechanical vibration of the device to provide tactile feedback require two separate systems to detect touch input and to provide tactile feedback to the user. The TSTF layer 132 is able to provide both of these functionalities through the same hardware. Consequently, the bill of materials can be reduced.

Tactile stimulation can also be used to convey tactile information to the user in accordance with images displayed on the display panel 130. For example, if a selectable option, for example a soft key, is displayed on the display panel 130, electrodes 136 in the TSTF layer 132 corresponding to the location of the selectable option on the display panel 130 may be activated. In this way, when the user's finger comes into contact with an area of the surface of the TSTF layer 132 that corresponds to the selectable option, the nerve receptors in the finger tip will be stimulated by the activated electrode 136, thereby indicating to the user that their finger tip is in a position corresponding to the selectable option. Other areas are not energised, so a finger tip in another area would not be stimulated.

A selectable option may be displayed on the display panel 130 as a region of a particular colour, brightness or pattern bounded by a region of a different colour, brightness or pattern. Alternatively, in the case of a link in an internet browser, for example, there may be a different type of visible definition between the option and the surrounding region. A link may be represented on a display as, for example, a word, a phrase, a sentence, or a URL. The text of the link may be in a particular colour, with the background being in a different colour. Alternatively or in addition the text of the link may be underlined.

It will be understood that, if a touch input is applied to the TSTF layer 132 in a region corresponding to the text, the link will be selected. However, there may also be a small region of the background region surrounding the link that, if selected by touch input, also causes the link to be followed. In any case, whether the boundary between a selectable option is clearly visible to the user or not, the processor that controls the display panel 130 and the TSTF layer 132 still defines a boundary, the region inside which corresponds to a selectable option, and the region outside of which does not.

The electrodes 136 of the TSTF layer 132 that correspond to the region of display panel 130 that is within the boundary of the selectable option may be activated to indicate to the user that their finger is in contact with a region of the TSTF layer that corresponds to a selectable option on the display screen. In this way, the boundary determines which electrodes 136 of the TSTF layer 132 are to be activated. It will be understood that more than one selectable option may be displayed on the display panel 130 simultaneously. In this case, plural boundaries define plural regions of activated electrodes 136.

The object displayed on the display panel may not represent a selectable option. Instead, it may represent another object. For example the object may be an icon, a sprite, or such like. The tactile feedback in this case may indicate to a user that they have located the object, for instance so that they know that they can drag the object to a different location on the display.

The above functionality may also be implemented in dynamic situations, for example, where a moving image is displayed on the display panel 130. For example, if a moving image of a ripple is being displayed by the display panel 130, the electrodes which, at any given moment, correspond to the locations of the peaks of the capillary waves of the ripple may be activated to provide stimulation of the finger tip receptors. Consequently, the receptors in a user's fingertip are stimulated as the peaks of the capillary waves of the ripple appear to 'pass under' the fingertip, thereby providing a "haptic illusion". In order to maximise energy efficiency, only those electrodes which correspond to the locations of the peaks of the capillary waves of the ripple and which are detected as being under a user's fingertip may be activated.

In dynamic situations, a boundary is also defined. The boundary may not define a selectable region, but may instead define an object, for example the capillary wave discussed above. In the case of the capillary wave, two boundaries, an inner boundary and an outer boundary, may define the region of activation. When the object moves around the display panel 130, the boundary or boundaries also move. In this way, the locations at which the electrodes are activated changes as the boundary or boundaries move.

It will be understood that the level of activation of the electrodes 136 defined by the boundary or boundaries may not be uniform. For example, the electrodes corresponding to the peak of the capillary wave may have a higher level of activation, whereas those electrodes closer to the boundaries may have a lower level of activation. In any case, it will be understood the electrodes 136 outside the activated region defined by the boundary or boundaries are not activated, whereas those electrodes inside the region defined by the boundary or boundaries are activated.

TENS can be used to induce any tactile effect required, for example friction, roughness, steps in profile etc. The tactile stimulation pattern may thus be optimised to convey to the user an overall illusion of touching a physical key or button with features that are in relief with respect to the remaining surface. For example, a button in relief may be simulated using the TSTF layer by activating the electrodes to simulate two distinct regions of increased surface roughness, surrounding a region of less surface roughness. When a finger is moved across these regions the effect experienced may be similar to that of a finger being moved over a button in relief.

The electrodes 136 that correspond to a selectable option (or a moving image on the display panel 130) may not always be the electrodes that are immediately above the pixels on the display panel 130 that depict the selectable option. Instead, the electrodes may be slightly offset from the image of the selectable option. This compensates for the fact that the user may not be viewing the display 102 from directly above, but may be viewing instead from an angle less than 90 degrees from the plane of the display 102. The processor 128 may be operable to compensate for this offset by activating the electrodes in the area of the TSTF layer 132 that the user perceives to be directly above the image of the selectable option and not those electrodes which are actually directly above. It will be understood that there may be significant overlap between the area the user perceives to be directly above the image of the selectable option, and the area that is actually above the selectable option.

Highly pixelated tactile stimuli, such as that provided by the TSTF layer 132, can be used to provide a broad set of meaningful information for helping a user's finger to navigate the display 102. This results in improved user-device interaction and improved user satisfaction. Information can be conveyed to a user, via the TSTF layer 132, in a number of ways. For example, an electro-tactile stimulation language may be provided. For instance, combinations of short and long periods of stimulations may each have different, pre-determined meanings, for instance individual characters.

Alternatively, the electro-tactile stimulation language may utilise one or more of various parameters available to it to convey other messages to a user. These parameters may include, but are not limited to, stimulation frequency, pulse structure, pulse train pattern, signal modulation amplitude and signal intensity.

Different types of selectable option being displayed on the display panel may have different electrode activation patterns associated with them. For example, the electrodes 136 corresponding to a "DELETE" or a "RESET FACTORY SETTINGS" option, which when executed may cause an irreversible action to be performed, may have an associated activation pattern that is designed to alert the user of the serious consequences of the option. Such a pattern may include, for example, brief periods of particularly intense activation periodically separated by brief periods of no activation. Less potentially serious options, for example, links on a web page, may have a less intense and continuous electrode activation pattern associated with them.

Some suitable activation patterns will now be discussed. A first pattern may comprise alternate activation of a certain intensity and zero activation or substantial equal duration, similar to a square wave. Variations of the first pattern include different frequencies of the square wave. A second pattern may comprise alternate activation of a certain intensity and zero activation of dissimilar duration, similar to a square wave with a non-unity mark-to-space ratio. Variations of the second pattern include different frequencies and/or different mark-to-space ratios. A third pattern may include gradated transitions between full activation and zero activation. The gradated transitions may be ramping up and/or ramping down. The gradated transitions may involve curved ramping profiles, such as sine wave profiles. Variations of the second pattern include different frequencies and/or different gradients and/or different ramping profiles on leading and falling edges.

Instead of the electrode activation pattern being associated with the potential severity of a selectable option, the same activation pattern may be associated with the same type of option, regardless of the consequence of selecting it. For example, a "YES" option may have the same associated electrode activation pattern, regardless of whether its selection will result in the phone memory being deleted or it will cause a call to be commenced. In this way, over time, a user may learn to associate a particular activation pattern with a particular option.

Figure 5:
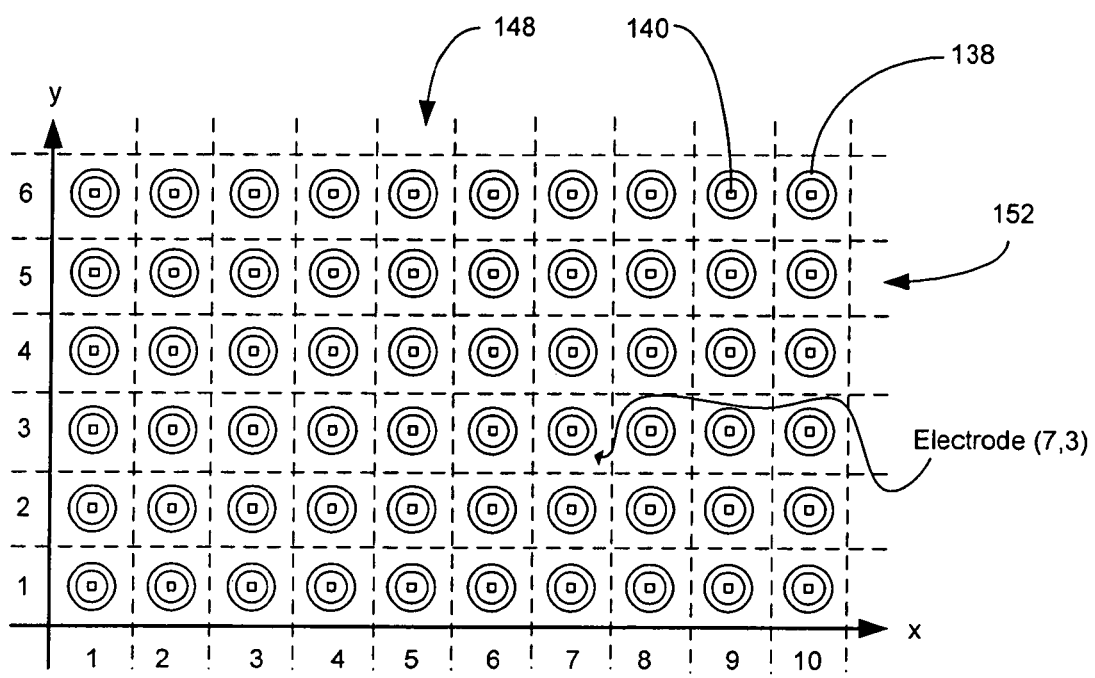
FIG. 5 is a schematic plan view of a portion of the component of FIG. 2.

The operability of the TSTF layer 132 to provide localised tactile feedback to a user will now be described with reference to FIG. 5. FIG. 5 depicts a schematic of a portion of the TSTF layer 132 comprising a 10×6 array of electrodes 136. The array of electrodes comprises six rows 152 of connected second electrode elements 140 and ten columns 148 of connected first electrode elements 138. In the Figure, each of the columns has been allocated an x-coordinate, the left hand (first) column being x=1 and the right hand (tenth) column being x=10. Each row has been allocated a y-coordinate, the lowermost (first) row in FIG. 5 being y=1 and the uppermost (sixth) row being y=6. In this way it is possible to identify each of the electrodes 136 based on the row and column of their constituent first and second electrode elements 138, 140. An electrode 136 having its first electrode element 138 in column x=7 and its second electrode element 140 in row y=3 may be identified as electrode (7, 3). In general, an electrode at any point in the array may be identified as electrode (x, y).

In order to activate a particular one of the electrodes 136, for example electrode (x=i, y=j), a potential of −V (relative to an intermediate potential within the device 10) is applied across the connected first electrode elements 138 in column x=i, and a potential +V (relative to an intermediate potential within the device 10) is applied across the connected second electrode elements 140 in row y=j. Consequently, the potential difference between the first and second electrode elements 138, 140 that constitute electrode (x=i, y=j) is 2×V. Each of the electrodes (x=i, y≠j), having a first electrode element 138 in column x=i and second electrode element in row y≠j, have a potential difference between their first and second electrode elements 138, 140 of +V. Each of the electrodes (x≠i, y=j), having a first electrode element 138 in column x≠i and second electrode element 140 in row y=j, have a potential difference between their first and second electrode elements 138, 140 of −V.

A potential difference of 2×V provides an electrical stimulation to user's finger tip that is above the threshold, $V_{th}$, for nervous stimulation. A potential difference of +/−V, however, provides an electrical stimulus that is beneath the threshold. The activated electrode (x=i, y=j), therefore, causes stimulation of the receptors in the user's finger, while all un-activated electrodes do not. $V_{th}$ may be in the range of 1-10 volts. The magnitude V of the potential supplied to each electrode element may be adjustable by a user of the device. In this way, the user can adjust the potential difference between electrode elements of an activated electrode in accordance with their individual threshold for nervous stimulation $V_{th}$.

It will be understood that, using the above method, any number of electrodes 136 can be activated at any one time.

Usually, in order to be able to individually activate the electrodes in an N×N array, each electrode would require a connection to a power supply. Thus, $N^2$ sets of connections would be required. By using the above method to individually activate the electrodes, however, only 2N sets of connections are required. If we consider a display having a square visible surface of side length 10 cm, and having a TSTF layer 132 with electrode spacing of 0.5 mm, then N=200. Therefore, $N^2=40000$, and 2N=400. Consequently, by utilising a system in accordance with the above embodiments, 100 times fewer (i.e. 1/100th the number of) sets of connections are required. This results in circuitry of a substantially simpler nature.

It will be understood that the electrodes 136 alternatively may be completely electrically independent from one another. Electrodes arranged thus may be individually activated using an active matrix addressing technique. In these embodiments, each electrode is provided with dedicated first and second connectors, instead of sharing connectors with other electrodes. Such embodiments have, for a given number of electrodes, an increased number of connectors.

The above method for activating a particular electrode is described with reference to DC potentials. However, it may be advantageous to use instead an AC potential.

The electrode addressing method described above also works in an AC case, but the AC case enables the modulation of the peak intensity experienced at the activated electrode by altering the relative phase of the waveforms applied to the row or rows 152 and column or columns 148 of the activated electrode or electrodes. Furthermore, tactile sensitivity in nerve receptors is a function of the frequency of the applied stimulus. Thus, the frequency response of the system can be tuned to generate the optimal tactile sensation. The optimum frequency may be in the range of 100-300 Hz. The frequency may instead be in the range 100 to 500 Hz. Suitable frequencies may be in the range 10 Hz to 3 kHz. The frequency may be user-definable. In this way, the frequency can be optimised in accordance with the tactile sensitivity of the user.

Figure 6:
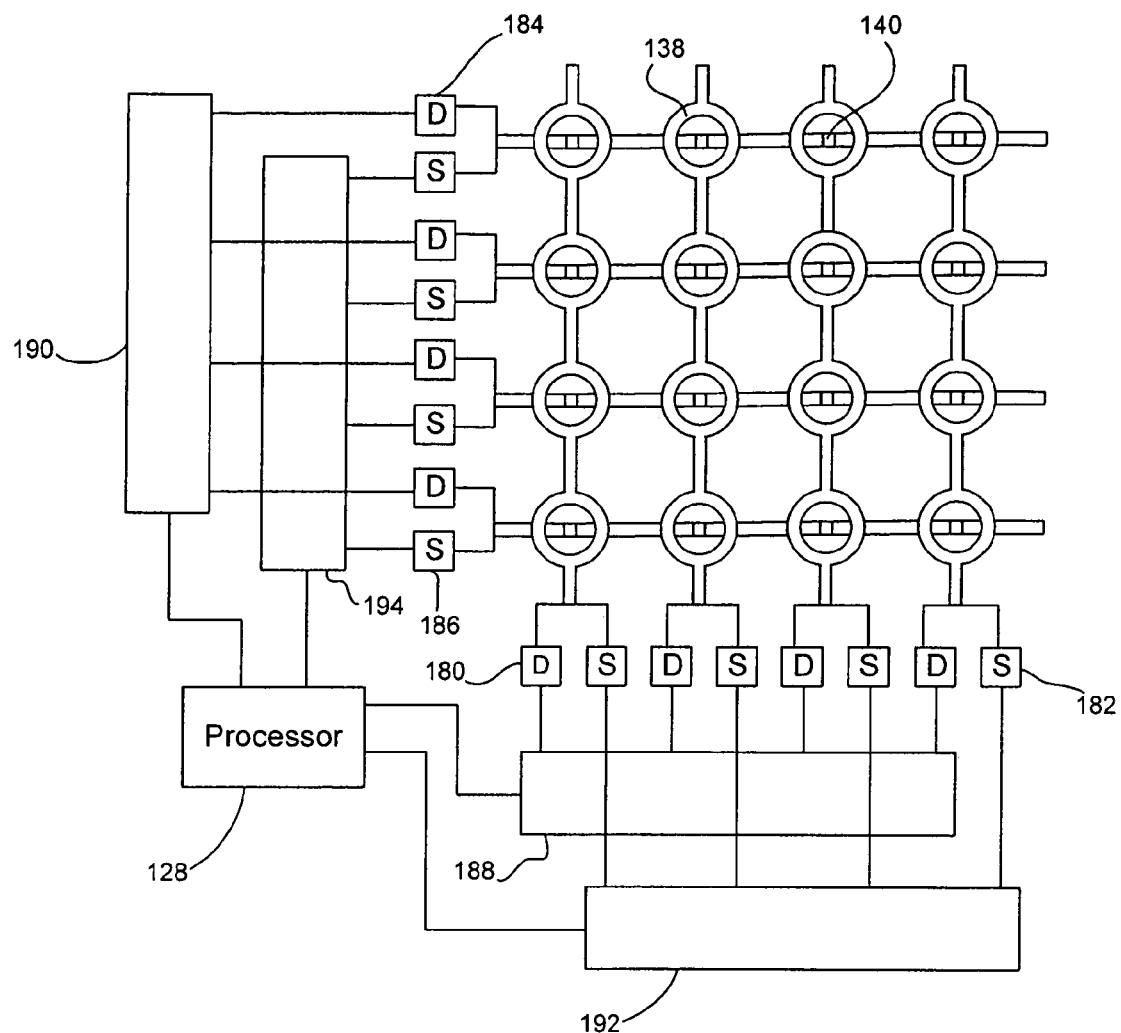
FIG. 6 is a schematic of circuitry for controlling a portion of the electrodes of FIG. 2.

FIG. 6 is schematic of circuitry for operating a portion of the TSTF layer 132. FIG. 6 shows a portion of the TSTF layer comprising a 4×4 array of electrodes 136, although it will be appreciated that this is merely exemplary.

Each column 148 of connected first electrode elements 138 is in connection with a respective detection sub-circuit 180 and with a respective stimulation sub-circuit 182. Each row 152 of connected second electrode elements 140 is in connection with a respective detection sub-circuit 180 and with a respective stimulation sub-circuit 182.

Each detection sub-circuit 180 relating to a column 148 of first electrode elements 138 is in connection with a first detection MUX 188. Each of the detection sub-circuits 180 relating to a row 152 of second electrode elements 140 is in connection with a second detection MUX 190.

Each stimulation sub-circuit 182 relating to a column 148 of first electrode elements 138 is in connection with a first stimulation MUX 192. Each of the stimulation sub-circuits 182 relating to a row 152 of second electrode elements 140 is in connection with a second stimulation MUX 194.

The first and second detection MUXes 188, 190 and the first and second stimulation MUXes 192, 194 are connected to the processor. The processor controls the stimulation MUXes and, indirectly, the stimulation circuits, such as to provide stimulation potentials at desired electrodes at desired times. The processor controls the detection MUXes so as to determine which electrodes are proximal to a user's finger tip.

Figure 7:
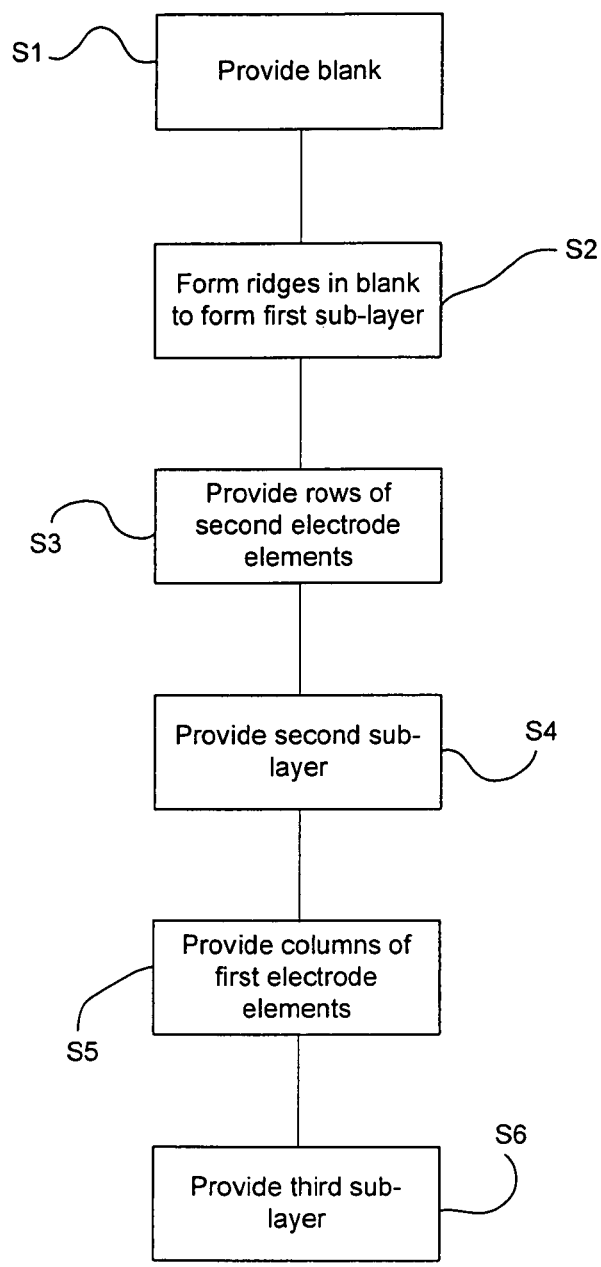
FIG. 7 is a flow chart depicting a method of manufacturing the component of FIG. 2.

FIG. 7 is a flow chart depicting a method of manufacturing the exemplary embodiment of the TSTF layer 132 described with reference to FIGS. 1 to 5.

In step S1, a blank for forming the first sub-layer 158 is provided. The blank comprises a pre-fabricated sheet of material having a main surface of a size substantially corresponding to a size of the display panel 130 with which the TSTF layer 132 is to be utilized. The thickness of the blank (i.e. the distance from the lower surface of the first sub-layer 158 to the upper surfaces 172 of plurality of ridges 168 in the finished sub-layer) may be in the micron to millimeter range. The blank may be comprise, for example, a transparent polymer such as silicone, polyimide, poly(methyl methacrylate) (acrylic glass), polystyrene, polycarbonate, polyethylene naphthalate, or polyethylene terephthalate.

In step S2, the ridges 168 are formed in the blank to create the first sub-layer 158. The ridges are provided by creating depressed regions in the surface of the blank. The depressed regions are provided at regular intervals across the surface of the blank. Each of the depressed regions extends across an entire length of the surface of the blank. The ridges 168 are the regions of the blank between the newly created depressed regions.

The depressed regions may be created by thermoplastic nanoimprint lithography (hot-embossing), photo nanoimprint lithography, electrochemical nanoimprinting, or any other suitable method of nanoimprinting.

In step S3, the rows 152 of connected second electrode elements 140 are provided on the upper surface of the first sub-layer 158. The rows 152 of connected second electrode elements 140 are provided at regular intervals across the upper surface of the first sub-layer 158. The rows 152 of connected second electrode elements 140 extend across an entire length of the upper surface of the first sub-layer 158. The longitudinal lengths of the rows 152 of connected second electrode elements 140 are substantially perpendicular to the longitudinal lengths of the ridges 168. Instead they may be non-perpendicular.

The rows 152 of connected second electrode elements 140 may be provided on the surface by CVD (chemical vapour deposition) in combination with an appropriately shaped mask. Alternatively, any other suitable technique may be used. Suitable techniques include, but are not limited to, physical vapour deposition (PVD), sputtering, spray-coating, evaporation, aerosol deposition via a shadow mask, other types of solution-phase deposition process, such as spin coating of a liquid nanocomposite or solution followed by lithographic or direct-write patterning, or doctor-blading.

In step S4, the second sub-layer 160 is provided on the upper surface of the first sub-layer 158 in the depressed regions between the between the ridges 168. The second sub-layer 160 extends to a height substantially level with the upper surfaces 172 of the ridges 168. The second sub-layer 160 encloses the second connecting elements 150 that connect the adjacent second electrode elements 140. Techniques that may be suitable for providing the second sub-layer 160 include, but are not limited to, PVD deposition, CVD deposition, sputtering, spraying, evaporation, a solution-phase deposition process, such as spin coating or doctor-blading, and hot lamination. The second sub-layer may comprise, for example, transparent silicone or of another appropriate material, such as poly(methyl methacrylate), polyimide, polystyrene, polycarbonate, polyethylene naphthalate, or polyethylene terephthalate.

In step S5, the columns 148 of connected first electrode elements 138 are provided on the upper surface of the second sub-layer 160. These are substantially perpendicular to the rows 152 of second electrode elements 140. Instead they may be non-perpendicular.

The columns 148 of connected first electrode elements 138 comprise an optically transparent material. Suitable materials include, but are not limited to, carbon nanotube networks (CNTNs), an indium-titanium-oxide (ITO) film, wide bandgap oxides, for example zinc oxide, provided in thin transparent layers, and thin layers of gold or silver.

The columns 148 of connected first electrode elements 138 may be provided using the same technique as that utilised to provide the rows 152 of second electrode elements 140.

In step S6, the third sub-layer 162 is provided. The third sub-layer encloses the electrode elements 138, 140 and the upper surface of the second sub-layer 160. The third sub-layer 162 comprise of silicone or of another appropriate material, such as poly(methyl methacrylate), polyimide, polystyrene, polycarbonate, polyethylene naphthalate, or polyethylene terephthalate. Techniques that may be suitable for providing the third sub-layer 162 include, but are not limited to, PVD deposition, CVD deposition, sputtering, spraying, evaporation, a solution-phase deposition process, such as spin coating or doctor-blading, and hot lamination.

Figure 8:
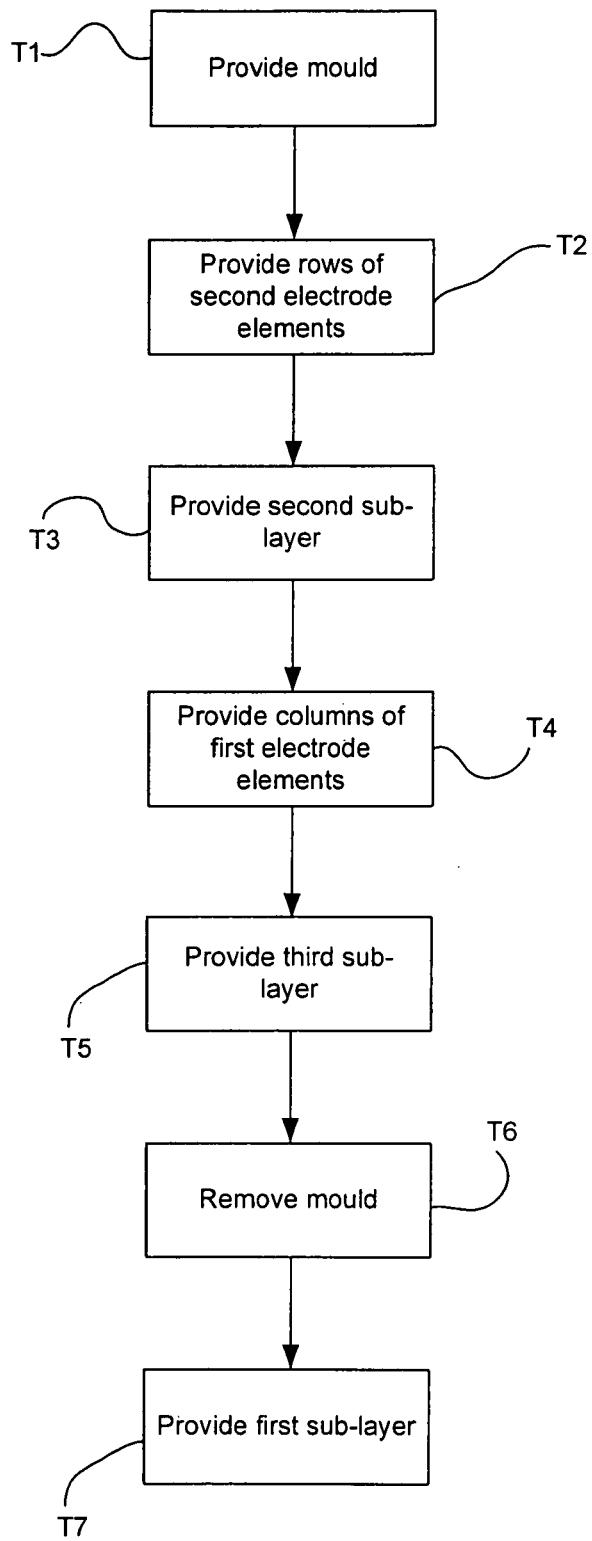
FIG. 8 is a flow chart depicting an alternative method of manufacturing the component of FIG. 2.

FIG. 8 depicts an alternative method of manufacturing the exemplary embodiment of the TSTF layer 132 described with reference to FIGS. 1 to 5. The method is similar to that described with reference to FIG. 7, the main difference being that the first sub-layer 158 is provided in a different manner. In step T1, a mould, having ridges and corresponding to the desired configuration of the first sub-layer 158, is provided.

In step T2, the rows 152 of connected second electrode elements 140 are provided on the surface of the mould. This may be carried out in the same way as step S3 of the previous method. In step T3, the second sub-layer 160, is provided. In step T4, the columns 148 of first electrode elements 138 are provided. In step T5, the third sub-layer is provided.

In Step T6, the mould is removed. In step T7, the first sub-layer 158 is provided by filling the region vacated by the removed mould.

Although all of the above is described with reference to a mobile phone, it will be understood that a TSTF layer 132 may be included in any device that requires touch-screen functionality. These devices include, but are not limited to, PDAs, media players, tablet computers, laptop computers, GPS navigation devices, and e-readers/books.

The nature and dimensions of the materials that constitute the TSTF layer 132, are selected so as to allow the TSTF layer 132 to be flexible. Consequently, the TSTF layer 132 is suitable for use with flexible display panels, such as flexible OLED displays, bistable displays, electrophoretic and electrowetting displays.

Suitable materials for the electrode elements are nanoparticle, nanowire, and nanorod based materials, solutions and composites. For instance, the electrode elements may incorporate nano-materials of any shape/morphology, sol-gel materials, or any other flexible, transparent material that exhibits conducting properties. Examples include carbon nanotube networks (CNTNs), an indium-titanium-oxide (ITO) film, wide bandgap oxides (such as zinc oxide) provided in thin transparent layers, and thin layers of gold or silver.

The sub-layers may comprise any suitable material composite consisting of a flexible, transparent host material (e.g. a transparent flexible polymer).

It will be realised that variations to the components and configuration described above may also be suitable. For example, each of the first electrode elements 138 may comprise another shape, for example, but not limited to, square, rectangular or hexagonal, having a vacant interior region in which the second electrode element 140 is located. Similarly, the second electrode elements 140 may have a different shape.

As an alternative to the first electrode element 138 surrounding the second electrode element 140, the first and second electrodes 138, 140 may merely be adjacent one another. In this example, the columns 148 of connected first electrode elements 138 may comprise lengths of optically transparent conducting material having a uniform width, extending across the surface of the second sub-layer 160.

It will be understood that the electrodes 136 still may be operable to provide transcutaneous electrical nervous stimulation, and to detect touch inputs, if the third sub-layer 162 is not included. In this embodiment, a user's finger tip would be in direct contact with the electrodes 136.

It will be understood that the touch sensitivity functionality of the device may be provided by the display panel 132 instead of or as well as the TSTF layer 132. Display panels that are capable of providing this functionality include, but are not limited to, capacitive touch sensitive display panels and resistive touch sensitive display panels.

Figure 9:
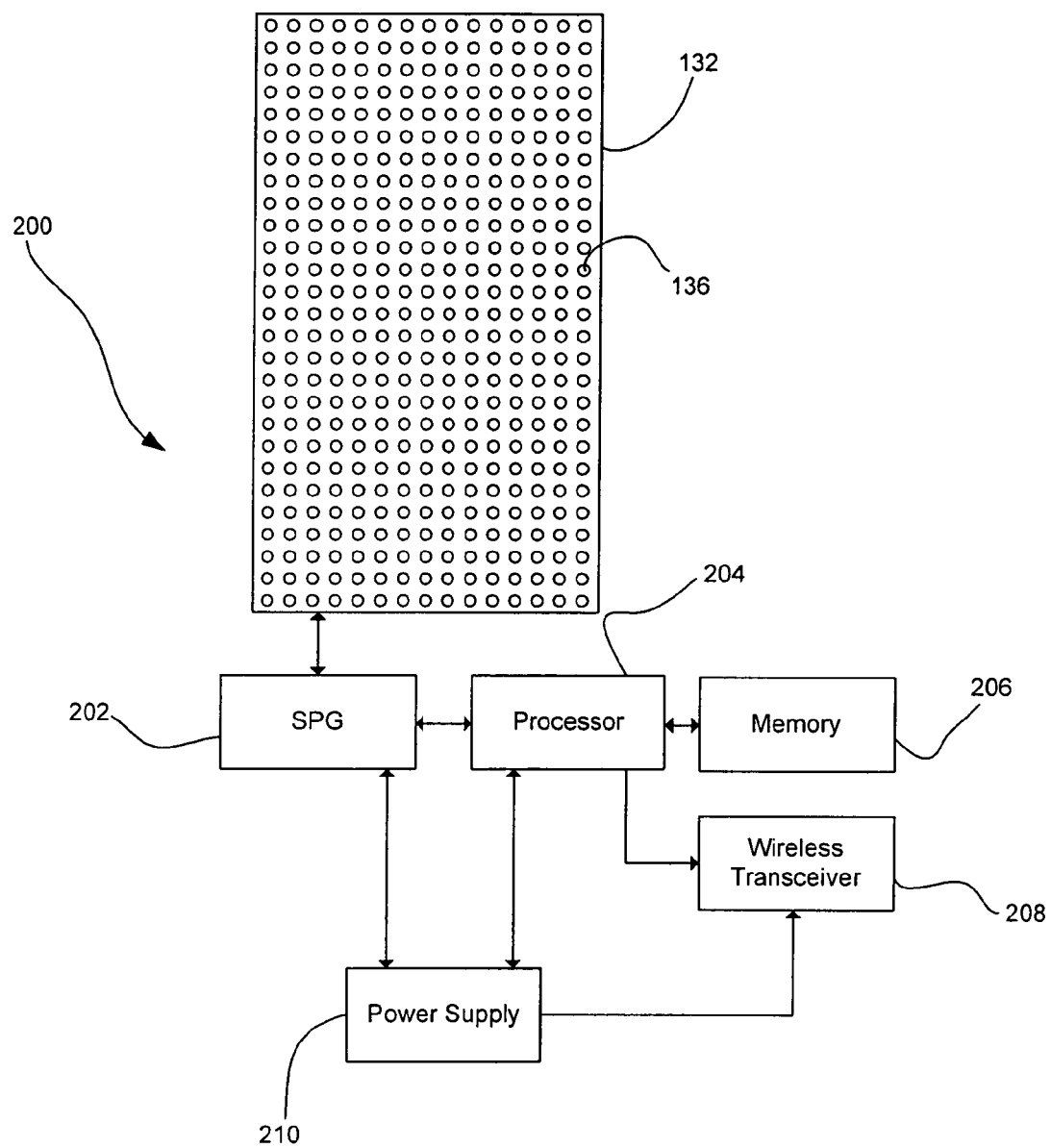
FIG. 9 is a schematic of a biomedical device.

FIG. 9 depicts a schematic of one embodiment of a biomedical device 200. The biomedical comprises a TSTF layer 132, a stimulation pattern generator (SPG) 202, a processor 204, memory 206, a wireless transceiver 208, and a power supply 210.

The biomedical device 200 may be operable to provide electromagnetic Field Therapy (EFT) to areas of the body with which the TSTF layer 132 is in contact. EFT may be beneficial in areas such as, but not limited to wound care, muscle strengthening, pain and inflammation relief, and bone growth and repair.

The biomedical device 200 may be operable also to sense neural, muscular and other biomedical activity.

The TSTF layer 132 comprises a two-dimensional array of electrodes 136. The TSTF layer 132 may be as described with reference to FIGS. 2 to 5. It may not be important whether the TSTF layer 132 is optically transparent, optically opaque, or translucent.

The electrodes 136 of the TSTF layer 132 alternatively may be completely electrically independent from one another. Electrodes arranged thus may be individually activated using an active matrix addressing technique. In these embodiments, each electrode is provided with dedicated first and second connectors, instead of sharing connectors with other electrodes.

By virtue of an insulating layer (not shown) uppermost in the TSTF layer 132, the biomedical device 200 may be operable to provide capacitively coupled EFT to areas of the body with which the TSTF layer 132 is in contact. Alternatively, no such insulating layer is present and there is direct coupling between electrodes and a user.

The electrodes 136 of the TSTF layer 132 may be in electrical connection with the SPG 202. The SPG 202 receives power from the power supply 210. The SPG is operable to generate nerve stimulation patterns for controlling the electrodes 136 of the TSTF layer 132. The SPG 202 may comprise an application specific integrated circuit (ASIC) (not shown) for generating the stimulation pattern. The SPG 202 may also comprise stimulation circuitry (not shown) suitable for activating the electrodes 136 based on the generated activation patterns. The stimulation circuitry may be the same as that described with reference to FIG. 6.

The SPG 202 may include also detection circuitry (not shown) suitable for detecting signals received by the electrodes 136 of the TSTF layer 132. The detection circuitry may be the same as that described with reference to FIG. 6.

The processor 204 is operable to control the operation of the SPG 202. It will be understood that the processor 204 may be integrated with the SPG 202. Signals detected by from the TSTF layer 132 via the SPG 202 may be stored in the memory 206 for transmission to another device at a later time. Alternatively or additionally the received signals may be transmitted to the other device (not shown) via the wireless transceiver 208 immediately following detection.

The wireless transceiver 208 may be operable also to receive signals from another device. The received signals may comprise signals for controlling the operation of the SPG 202 and/or the processor 204. The received signals may be stored in the memory for implementation by the processor 204 and the SPG 202 at a later time. Alternatively, they may implemented by the SPG 202 without first storing them in memory. The wireless transceiver 208 may be, for example, but not limited to a Bluetooth transceiver, another type of RF transceiver or an infra-red transceiver. Alternatively or additionally the device may be operable to receive or send signals to another device, via wired connection with the other device.

The power supply may be a battery, for example a small lightweight battery such as a paper battery or a watch battery. Alternatively the power supply may be connected to a mains electricity system.

The TSTF layer 132 may have a thin adhesive layer on the outer surface 116 of the third sub-layer 162 for affixing the TSTF layer to the skin of a patient. Alternatively, the TSTF layer 132 may be kept in contact with the skin of a user in another way, for example with medical tape applied over rear surface 166 of the first sub-layer 158.

The electrical components and circuitry, such as the SPG 202, the processor 204, the memory 206, the wireless transceiver 208 and the power supply 210 may provided on the rear surface 166 of the first sub-layer 158. In this way the biomedical device may be an unobtrusive and self-contained.

The TSTF layer may comprise the same materials as discussed previously in this specification. Consequently, the TSTF layer may be flexible. As such, the TSTF layer 132 may conform to the shape of the part of the user's body to which it is affixed.

The biomedical device 200 may be affixed to a user's skin over an area of the body requiring treatment or monitoring. For example, a patient requiring CCFET on their neck may wear the biomedical device to reduce pain without requiring the user to be physically attached to immovable equipment. The biomedical device 200 may be operable to provide CCFET in response to detected biomedical activity, such as detected muscle spasms. Also, when muscle spasms are detected in muscles underlying only a portion of the electrodes 136 in the TSTF layer 132, the biomedical device may be operable to activate only the portion of the electrodes. The electrodes 136 may be activated in the manner described with reference to FIG. 5.

It should be realised that the foregoing embodiments should not be construed as limiting. Other variations and modifications will be apparent to persons skilled in the art upon reading the present application. Moreover, the disclosure of the present application should be understood to include any novel features or any novel combination of features either explicitly or implicitly disclosed herein or any generalisation thereof and during the prosecution of the present application or of any application derived therefrom, new claims may be formulated to cover any such features and/or combination of such features.

What is claimed is:

1. Apparatus comprising:
    a visual display;
    at least one electrode; and
    an electrically insulating layer forming a portion of an exterior surface of said apparatus proximal to said at least one electrode;
    wherein the apparatus is a hand-held device, and the hand-held device is configured to house the visual display, the at least one electrode and the electrically insulating layer;
    wherein in combination the at least one electrode and the electrically insulating layer are configured to provide stimulation to a user by utilizing capacitive coupling, via the electrically insulating layer, between the electrode and a user contacting the portion of the exterior surface of said apparatus; and
    wherein the electrode comprises a first planar electrode element lying substantially in a first plane and extending across the first plane and a second planar electrode element lying substantially in a second plane and extending across the second plane, and wherein the first planar electrode element and the second planar electrode element are electrically insulated from one another.

2. The apparatus as claimed in claim 1, wherein the apparatus is configured to provide a time varying potential difference between the first electrode element and the second electrode element.

3. The apparatus as claimed in claim 2 wherein the potential difference is in the range 1 to 10 volts.

4. The apparatus of claim 1, wherein the electrode is optically transparent.

5. The apparatus of claim 1, wherein the exterior surface is hydrophobic and/or oleophobic.

6. The apparatus of claim 1, wherein the insulating layer has a thickness in the range 500 nm to 2 micrometers.

7. The apparatus of claim 1, comprising a plurality of separately controlled electrodes separated by a distance in the range 0.1 to 5 mm.

8. The apparatus of claim 1, wherein said electrode constitutes part of a two-dimensional array of optically transparent electrodes.

9. The apparatus of claim 1, wherein said apparatus is flexible.

10. The apparatus of claim 1, comprising a detection circuit configured to detect a user contacting and/or proximal to said portion of said exterior surface of said apparatus.

11. The apparatus of claim 8, comprising a stimulation circuit configured to provide a nerve stimulation potential at the electrode in response to a detection circuit detecting a user contacting said portion of said exterior surface of said apparatus proximal to said electrode.

12. The apparatus of claim 1 wherein the visual display underlies the electrode and the electrically insulating layer.

13. A method comprising:
    providing a visual display;
    controlling activation of at least one electrode to provide tactile stimulation to a user by utilizing capacitive coupling between the electrode and a user contacting a portion of an exterior insulating layer of an apparatus proximal to said at least one electrode,
    wherein the apparatus is a hand-held device, and the hand-held device is configured to house the visual display, the at least one electrode and the exterior insulating layer; and
    wherein the electrode comprises a first planar electrode element lying substantially in a first plane and extending across the first plane and a second planar electrode element lying substantially in a second plane and extending across the second plane and wherein the first planar electrode element and the second planar electrode element are electrically insulated from one another.

14. A method as claimed in claim 13 further comprising
prior to the controlling step, detecting when a user is contacting and/or proximal to said portion of said exterior surface of said apparatus.

15. Apparatus comprising:
at least one electrode; and
an electrically insulating layer forming a portion of an exterior surface of said apparatus proximal to said at least one electrode;
wherein in combination the at least one electrode and the electrically insulating layer are configured to provide stimulation to a user by utilizing capacitive coupling, via the electrically insulating layer, between the electrode and a user contacting the portion of the exterior surface of said apparatus; and
wherein the apparatus is a hand held device, and the hand-held device is configured to house the at least one electrode, the electrically insulating layer and a visual display underlying the at least one electrode and the electrically insulating layer.

16. The apparatus as claimed in claim 15 wherein the electrode comprises a first electrode element and a second electrode element electrically insulated from one another.

17. The apparatus of claim 15, wherein the electrode is optically transparent.

18. The apparatus of claim 15, wherein the exterior surface is hydrophobic and/or oleophobic.

19. The apparatus of claim 15, wherein the insulating layer has a thickness in the range 500 nm to 2 micrometers.

20. The apparatus of claim 15, comprising a plurality of separately controlled electrodes separated by a distance in the range 0.1 to 5 mm.

21. The apparatus of claim 15, wherein said electrode constitutes part of a two-dimensional array of optically transparent electrodes.

22. The apparatus of claim 15, wherein said apparatus is flexible.

23. The apparatus of claim 15, comprising a detection circuit configured to detect a user contacting and/or proximal to said portion of said exterior surface of said apparatus.

24. The apparatus of claim 15, comprising a stimulation circuit configured to provide a nerve stimulation potential at the electrode in response to a detection circuit detecting a user contacting said portion of said exterior surface of said apparatus proximal to said electrode.

25. The apparatus of claim 16 wherein the apparatus is configured to provide a time varying potential difference between the first electrode element and the second electrode element.

26. The apparatus as claimed in claim 25 wherein the potential difference is in the range 1 to 10 volts.

27. A method comprising:
controlling activation of at least one electrode to provide tactile stimulation to a user by utilizing capacitive coupling between the electrode and a user contacting a portion of an exterior insulating layer of an apparatus proximal to said at least one electrode,
wherein the apparatus is a hand held device, and the hand-held device is configured to house the at least one electrode, the electrically insulating layer and a visual display underlying the at least one electrode and the exterior insulating layer.

28. A method as claimed in claim 27 further comprising
prior to the controlling step, detecting when a user is contacting and/or proximal to said portion of said exterior surface of said apparatus.

29. Apparatus comprising:
a visual display;
at least one electrode;
an electrically insulating layer covering the at least one electrode and forming a portion of an exterior surface of said apparatus proximal to said at least one electrode; and
a stimulation circuit configured to control a time varying nerve stimulation potential difference at the electrode;
wherein the apparatus is a hand-held device, and the hand-held device is configured to house the visual display, the at least one electrode, the electrically insulating layer and the stimulation circuit; and
wherein in combination the at least one electrode and the electrically insulating layer are configured to provide stimulation to a finger of a user by utilizing capacitive coupling, via the electrically insulating layer, between the electrode and a user contacting the portion of the exterior surface of said apparatus.

30. The apparatus as claimed in claim 29, wherein the electrode comprises a first electrode element and a second electrode element electrically insulated from one another.

31. The apparatus as claimed in claim 30 wherein the potential difference is provided between the first and second electrode element and is in the range 1 to 10 volts.

32. The apparatus of claim 29, wherein the electrode is optically transparent.

33. The apparatus of claim 29, wherein the exterior surface is hydrophobic and/or oleophobic.

34. The apparatus of claim 29, wherein the insulating layer has a thickness in the range 500 nm to 2 micrometers.

35. The apparatus of claim 29, comprising a plurality of separately controlled electrodes separated by a distance in the range 0.1 to 5 mm.

36. The apparatus of claim 29, wherein said electrode constitutes part of a two-dimensional array of optically transparent electrodes.

37. The apparatus of claim 29, wherein said apparatus is flexible.

38. The apparatus of claim 29, comprising a detection circuit configured to detect a user contacting and/or proximal to said portion of said exterior surface of said apparatus.

39. The apparatus of claim 29 wherein the stimulation circuit provides the nerve stimulation potential difference in response to a detection circuit detecting a user contacting said portion of said exterior surface of said apparatus proximal to said electrode.

40. The apparatus of claim 29 wherein the visual display underlies the electrode and the electrically insulating layer.

41. A method comprising:
providing display;
controlling activation of at least one electrode to provide tactile stimulation to a finger of a user by utilizing capacitive coupling between the electrode and a user contacting a portion of an exterior insulating layer, covering the at least one electrode, of an apparatus proximal to said at least one electrode by controlling a time varying nerve stimulation potential difference at the electrode,
wherein the apparatus is a hand-held device, and the hand-held device is configured to house the visual display, the at least one electrode and the exterior insulating layer.

42. A method as claimed in claim 41 further comprising
prior to the controlling step, detecting when a user is contacting and/or proximal to said portion of said exterior surface of said apparatus.

43. Apparatus comprising:
a visual display;
at least one optically transparent electrode; and
an electrically insulating layer forming a portion of an exterior surface of said apparatus proximal to said at least one electrode;
wherein the apparatus is a hand-held device, and the hand-held device is configured to house the visual display, the at least one electrode and the electrically insulating layer;
wherein in combination the at least one electrode and the electrically insulating layer are configured to provide tactile feedback stimulation to a finger of a user by utilizing capacitive coupling, via the electrically insulating layer, between the electrode and the user, in response to the user contacting the portion of the exterior surface of said apparatus, by applying a potential difference to the electrode, and
wherein the potential difference is in the range 1 to 10 volts.

44. The apparatus as claimed in claim 43 wherein the electrode comprises a first electrode element and a second electrode element electrically insulated from one another.

45. The apparatus of claim 43, wherein the exterior surface is hydrophobic and/or oleophobic.

46. The apparatus of claim 43, wherein the insulating layer has a thickness in the range 500 nm to 2 micrometers.

47. The apparatus of claim 43, comprising a plurality of separately controlled electrodes separated by a distance in the range 0.1 to 5 mm.

48. The apparatus of claim 43, wherein said electrode constitutes part of a two-dimensional array of optically transparent electrodes.

49. The apparatus of claim 43, wherein said apparatus is flexible.

50. The apparatus of claim 43, comprising a detection circuit configured to detect a user contacting and/or proximal to said portion of said exterior surface of said apparatus.

51. The apparatus of claim 50, comprising a stimulation circuit configured to provide a nerve stimulation potential at the electrode in response to a detection circuit detecting a user contacting said portion of said exterior surface of said apparatus proximal to said electrode.

52. The apparatus of claim 43 where the visual display underlies the electrode and the electrically insulating layer.

53. The apparatus of claim 44 wherein the potential difference is a time varying potential difference between the first electrode element and the second electrode element.

54. A method comprising;
providing a visual display;
controlling activation of at least one optically transparent electrode to provide tactile feedback stimulation to a finger of a user by utilizing capacitive coupling, via an exterior insulating layer, between the electrode and the user, in response to the user contacting a portion of the exterior insulating layer proximal to said at least one electrode,
wherein the visual display, the at least one electrode and the exterior insulating layer are housed in a hand-held device;
wherein the electrode is activated by applying a potential difference in the range 1 to 10 volts.

55. A method as claimed in claim 54 further comprising
prior to the controlling step, detecting when a user is contacting and/or proximal to said portion of said exterior surface of said apparatus.

56. The apparatus of claim 1, wherein the first plane and the second plane are parallel.

* * * * *

UNITED STATES PATENT AND TRADEMARK OFFICE
CERTIFICATE OF CORRECTION

PATENT NO. : 8,805,517 B2  
APPLICATION NO. : 12/316465  
DATED : August 12, 2014  
INVENTOR(S) : Radivojevic et al.

It is certified that error appears in the above-identified patent and that said Letters Patent is hereby corrected as shown below:

In the Claims

Claim 41, col. 20, line 52 --visual-- should be inserted in between "providing" and "display".

Signed and Sealed this
Fourth Day of November, 2014

Michelle K. Lee
*Deputy Director of the United States Patent and Trademark Office*